(12) United States Patent
Uehara

(10) Patent No.: US 8,728,450 B2
(45) Date of Patent: May 20, 2014

(54) HAIR CONDITIONING COMPOSITION COMPRISING QUATERNIZED SILICONE POLYMER, GRAFTED SILICONE COPOLYOL, AND DIALKYL CATIONIC SURFACTANT

(75) Inventor: Nobuaki Uehara, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 875 days.

(21) Appl. No.: 12/124,710

(22) Filed: May 21, 2008

(65) Prior Publication Data

US 2008/0292575 A1 Nov. 27, 2008

Related U.S. Application Data

(60) Provisional application No. 60/931,413, filed on May 23, 2007.

(51) Int. Cl.
| | |
|---|---|
| *A61Q 5/02* | (2006.01) |
| *A61Q 5/12* | (2006.01) |
| *A61K 8/00* | (2006.01) |
| *A61K 8/18* | (2006.01) |
| *A61Q 5/00* | (2006.01) |
| *A61Q 9/00* | (2006.01) |
| *A61K 8/72* | (2006.01) |
| *A61Q 7/00* | (2006.01) |

(52) U.S. Cl.
USPC ............... 424/70.122; 424/70.1; 424/70.11; 424/70.12

(58) Field of Classification Search
USPC ...................................... 424/70.12
See application file for complete search history.

(56) References Cited

U.S. PATENT DOCUMENTS

2007/0041929 A1* 2/2007 Torgerson et al. ....... 424/70.122

FOREIGN PATENT DOCUMENTS

| GB | 2254325 A | * 10/1992 | ............ C07C 211/63 |
|---|---|---|---|
| WO | WO 2006/138201 | 12/2006 | |

OTHER PUBLICATIONS

"Personal Care Product Guide", 2002, Akzo Nobel Surface Chemistry LLC, pp. 1-16.*

* cited by examiner

*Primary Examiner* — Gina C Justice
*Assistant Examiner* — Michael B Pallay
(74) *Attorney, Agent, or Firm* — Linda M. Sivik

(57) ABSTRACT

Disclosed is a hair conditioning composition comprising: (a) a quaternized silicone polymer; (b) a grafted silicone copolyol; (c) a cationic surfactant system comprising a dialkyl quaternized ammonium salt cationic surfactant; (d) a high melting point fatty compound; and (e) an aqueous carrier. The present invention can provide improved conditioning benefits such as smooth feel and reduced friction in conditioning compositions using dialkyl quaternized ammonium salt cationic surfactants.

7 Claims, No Drawings

HAIR CONDITIONING COMPOSITION COMPRISING QUATERNIZED SILICONE POLYMER, GRAFTED SILICONE COPOLYOL, AND DIALKYL CATIONIC SURFACTANT

CROSS REFERENCE TO RELATED APPLICATION

This application claims the benefit of U.S. Provisional Application No. 60/931,413, filed May 23, 2007.

FIELD OF THE INVENTION

The present invention relates to a hair conditioning composition comprising: (a) a quaternized silicone polymer; (b) a grafted silicone copolyol; (c) a cationic surfactant system comprising a dialkyl quaternized ammonium salt cationic surfactant; (d) a high melting point fatty compound; and (e) an aqueous carrier. The present invention provide improved conditioning benefits such as smooth feel and reduced friction in conditioning compositions using dialkyl quaternized ammonium salt cationic surfactants.

BACKGROUND OF THE INVENTION

Human hair becomes soiled due to its contact with the surrounding environment and from the sebum secreted by the scalp. The soiling of hair causes it to have a dirty feel and an unattractive appearance. The soiling of the hair necessitates shampooing with frequent regularity.

Shampooing cleans the hair by removing excess soil and sebum. However, shampooing can leave the hair in a wet, tangled, and generally unmanageable state. Once the hair dries, it is often left in a dry, rough, lusterless, or frizzy condition due to removal of the hair's natural oils and other natural conditioning and moisturizing components. The hair can further be left with increased levels of static upon drying, which can interfere with combing and result in a condition commonly referred to as "fly-away hair," or contribute to an undesirable phenomenon of "split ends." Further, chemical treatments, such as perming, bleaching, or coloring hair, can also damage hair and leave it dry, rough, lusterless, and damaged.

A variety of approaches have been developed to condition the hair. A common method of providing conditioning benefits to the hair is through the use of conditioning agents such as cationic surfactants and polymers, high melting point fatty compounds, low melting point oils, silicone compounds, and mixtures thereof.

However, there still exists a desire for hair conditioning compositions which provide improved conditioning benefits such as smooth feel and reduced friction. A variety of approaches have been developed to obtain such conditioning benefits For example, PCT publication WO2006/138201 discloses a hair conditioning composition comprising a silicone polymer containing quaternary groups and a gel matrix, the gel matrix comprising a cationic surfactant, high melting point fatty compound, and an aqueous carrier in claim 1. PCT publication WO2006/138201 also discloses, in Examples, the hair conditioning compositions in which the cationic surfactant is Behenyl trimethyl ammonium methylsulfate/chloride and which further contain SF1488 silicone copolyol.

However, there remains a need for hair conditioning compositions which provide improved benefits such as reduced friction in a variety of gel matrixes such as those using a different cationic surfactant.

Additionally, there also exists a need for hair conditioning compositions which provide clean feel and/or reduced tacky/heavy feel, while providing such improved conditioning benefits. Regarding such clean feel and/or reduced tackiness, there exists a need for hair conditioning compositions providing such benefits on both wet and dry hair. Clean feel and/or reduced tackiness on wet hair include, for example, ease-to-rinse feel. Ease-to-rinse feel are, for example, fast reduced slippery feel, and/or increased clean feel after starting to rinse the hair. Such reduced slippery feel, and/or increased clean feel can be a signal for consumers to stop rinsing the hair conditioning compositions, while remaining sufficient amount of deposition of conditioning agents on the hair.

None of the existing art provides all of the advantages and benefits of the present invention.

SUMMARY OF THE INVENTION

The present invention is directed to a hair conditioning composition comprising by weight.
(a) from about 0.1% to about 15% of a silicone polymer containing quaternary groups wherein said silicone polymer comprises silicone blocks with greater than about 200 siloxane units;
(b) a grafted silicone copolyol at a level such that the weight % of the granted silicone copolyol in its mixture with the quaternized silicone polymer is in the range of from about 1% to about 50%;
(c) from about 0.1% to about 10% by weight of the composition of a cationic surfactant system comprising a dialkyl quaternized ammonium salt cationic surfactant;
(d) from about 1% to about 20% by weight of the composition of a high melting point fatty compound; and
(e) an aqueous carrier.

The present invention provide improved conditioning benefits such as smooth feel and reduced friction in conditioning compositions using dialkyl quaternized ammonium salt cationic surfactants. Additionally, the conditioning compositions of the present invention can provide clean feel and/or reduced tacky/heavy feel, while providing such improved conditioning benefits.

These and other features, aspects, and advantages of the present invention will become better understood from a reading of the following description, and appended claims.

DETAILED DESCRIPTION OF THE INVENTION

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixtures" is meant to include a simple combination of materials and any compounds that may result from their combination.

Composition

It is believed that; by the use of grafted silicone copolyol at a specific level, together with the quaternized silicone polymer, the present invention provides improved conditioning benefits such as smooth feel and reduced friction in conditioning compositions using dialkyl quaternized ammonium salt cationic surfactants.

Preferably, the composition of the present invention is substantially free of anionic surfactants and anionic polymers, in view of stability of the gel matrix. In the present invention, "substantially free of anionic surfactants and anionic polymers" means that the composition contains 1% or less, preferably 0.5% or less, more preferably totally 0% of total of anionic surfactants and anionic polymers.

Quaternized Silicone Polymer

The compositions of the present invention comprise a silicone polymer containing quaternary groups. The quaternized silicone polymer provides improved conditioning benefits such as smooth feel, reduced friction, prevention of hair damage. Especially, the quaternary group can have good affinity with damaged/colorant hairs. The quaternized silicone polymer is present in an amount of from about 0.1% to about 15%, preferably from about 0.2% to about 10%, more preferably from about 0.3% to about 5%, and even more preferably from about 0.5% to about 4% by weight of the composition.

The silicone polymer of the present invention is comprised of at least one silicone block and at least one non-silicone block containing quaternary nitrogen groups, wherein the number of the non-silicone blocks is one greater than the number of the silicone blocks. The silicone polymers correspond to the general structure (I):

$$A^1\text{-}B\text{-}(A^2\text{-}B)_m\text{-}A^1 \quad (I)$$

wherein,
B is the silicone blocks with greater than 200 siloxane units;
$A^2$ is the non-silicone blocks containing quaternary nitrogen groups;
$A^1$ are end groups which may contain quaternary groups; and
m is an integer 0 or greater, with the proviso that if m=0 then the $A^1$ groups contain quaternary groups.

Structures corresponding to the general formula, for example, are disclosed in U.S. Pat. No. 4,833,225, in U.S. Patent Application Publication No. 2004/0138400, and in U.S. Patent Application Publication No. 2004/0048996.

In one embodiment, the silicone polymers can be represented by the following structure (II)

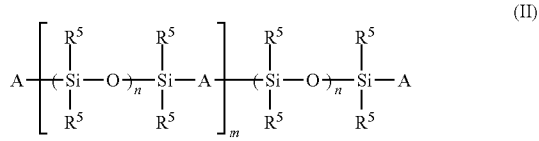

wherein,
A is a group which contains at least one quaternary nitrogen group, and which is linked to the silicon atoms of the silicone block by a silicon-carbon bond, each A independently can be the same or different;
$R^5$ is an alkyl group of from about 1 to about 22 carbon atoms or an aryl group; each $R^5$ independently can be the same or different;
m is an integer of from 0 or greater, preferably m is less than 20, more preferably m is less than 10; and
n is an integer greater than about 200, preferably greater than about 250, more preferably greater than about 300; preferably less than about 700, more preferably less than about 500.

A preferred structure (III) is with $R^5$ as methyl,

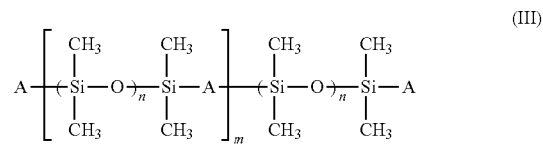

wherein,
A is a group which contains at least one quaternary nitrogen group and is linked to the silicone atoms of the silicone block by a silicon-carbon bond, each A independently can be the same or different;
m is an integer of from 0 or greater, preferably m is less than 20, more preferably m is less than 10;
and n is an integer greater than about 200, preferably greater than about 250, more preferably greater than about 300; preferably less than about 700, more preferably less than about 500.

In another embodiment, the repeat unit of the silicone polymers (the ($A^2$-B) repeat unit in structure (I)) can be represented by the following structure (IV):

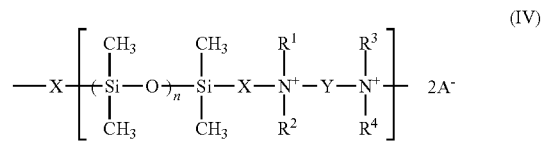

wherein.
X is a bivalent hydrocarbon radical with at least about 4 carbon atoms, which contains a hydroxyl group and can be interrupted by an oxygen atom, and the groups X in the repetition units can be the same or different;
Y is a bivalent hydrocarbon radical with at least about 2 carbon atoms, which can contain a hydroxyl group and which can be interrupted by one or more oxygen or nitrogen atoms, preferably one oxygen atom or one nitrogen atom;
$R^1$, $R^2$, $R^3$, and $R^4$ are the same or different and represent a hydrogen or alkyl groups with from about 1 to about 4 carbon atoms or benzyl groups; in one embodiment, the groups $R^1$ and $R^3$, or $R^2$ and $R^4$ are components of a single alkylene group which connects the two $N^+$ atoms;
$A^-$ is an inorganic or organic anion;
n is an integer greater than about 200, preferably greater than about 250, more preferably greater than about 300; preferably less than about 700, more preferably less than about 500.

In another embodiment, the $A^1\text{-}B\text{-}(A^2\text{-}B)_m\text{-}A^1$ silicone block copolymer can be described as a polysiloxane compound containing:

a) at least one polyalkylene oxide structural unit with the general structures (V-VIII):

-A-E-;   (V)

-E-A-:   (VI)

-A-E-A'-; and/or   (VII)

A'-E-A-.   (VIII)

wherein,
A is selected from the group consisting of —CH$_2$C(O)O—, —CH$_2$CH$_2$C(O)O—, —CH$_2$CH$_2$CH$_2$C(O)O—, —OC(O)CH$_2$—, —OC(O)CH$_2$—, —OC(O)CH$_2$CH$_2$—, and —OC(O)CH$_2$CH$_2$CH$_2$—;
A' is selected from the group consisting of —CH$_2$C(O)—, —CH$_2$CH$_2$C(O)—, —CH$_2$CH$_2$CH$_2$C(O)—, —C(O)CH$_2$—, —C(O)CH$_2$—, —C(O)CH$_2$CH$_2$—, and, —C(O)CH$_2$CH$_2$CH$_2$—;

E is a polyalkylene oxide group selected from the group consisting of —[CH$_2$CH$_2$O]$_q$-[CH$_2$CH(CH$_3$)O]$_r$—, and, —[OCH(CH$_3$)CH$_2$]$_r$-[OCH$_2$CH$_2$]$_q$—; wherein q is from about 1 to about 200; wherein r is from about 0 to about 200.

wherein,
the terminal position oxygen atom of A binds to the terminal position —CH$_2$— group of E, and the terminal position carbonyl carbon atom of A' binds to the terminal position oxygen atom of E forming ester groups in each case, and/or at least one terminal position polyalkylene oxide structural unit of the structure (IX)

 (IX)

wherein,
A and E are the same as above; and
R$^2$ is H, straight chain, cyclical or branched C$_1$ to C$_{20}$ hydrocarbon group, which can be interrupted by —O—, or —C(O)— and substituted with —OH, and can be acetylene, olefinic, or aromatic;

b) at least one bivalent or trivalent organic group which contains at least one ammonium group;

c) at least one polysiloxane structural unit with the general structure (X)

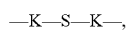 (X)

wherein,
S conforms to the following structure (XI)

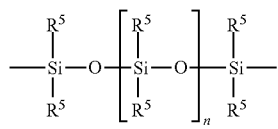 (XI)

wherein,
R$^5$ is an alkyl group of from about 1 to about 22 carbon atoms or an aryl group, and wherein each R$^5$ independently can be the same or different,
n is an integer greater than about 200, preferably greater than about 250, more preferably greater than about 300; preferably less than about 700, more preferably less than about 500.

The S groups can be the same or different if several S groups are present in the polysiloxane compound.

K in structure (X) is a bivalent or trivalent straight chain, cyclical, or branched C$_2$ to C$_{40}$ hydrocarbon group which is interrupted by —O—, —NH—, —NR$^5$—, —C(O)—, —C(S)—,

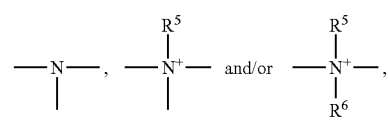

and is substituted by OH;
wherein,
R$^5$ is as defined above in structure (XI), or represents a bond to a bivalent group R$^6$;
wherein,
R$^6$ represents a monovalent or bivalent straight chain, cyclical or branched C$_1$ to C$_{20}$ hydrocarbon group which is interrupted by —O—, —NH—, —C(O)—, or —C(S)— and can be substituted with —OH or -A-E-R$^2$ wherein A, E, and R$^2$ are defined as in structure (IX) above.

The K groups can be identical or different from each other, and in the event K represents a trivalent group, the saturation of the third valence takes place through a bonding to the above mentioned organic group which contains at least one ammonium group;

d) at least one organic or inorganic acid group for neutralization of the charges resulting from the ammonium groups.

A more preferred embodiment is the following structure (XII)

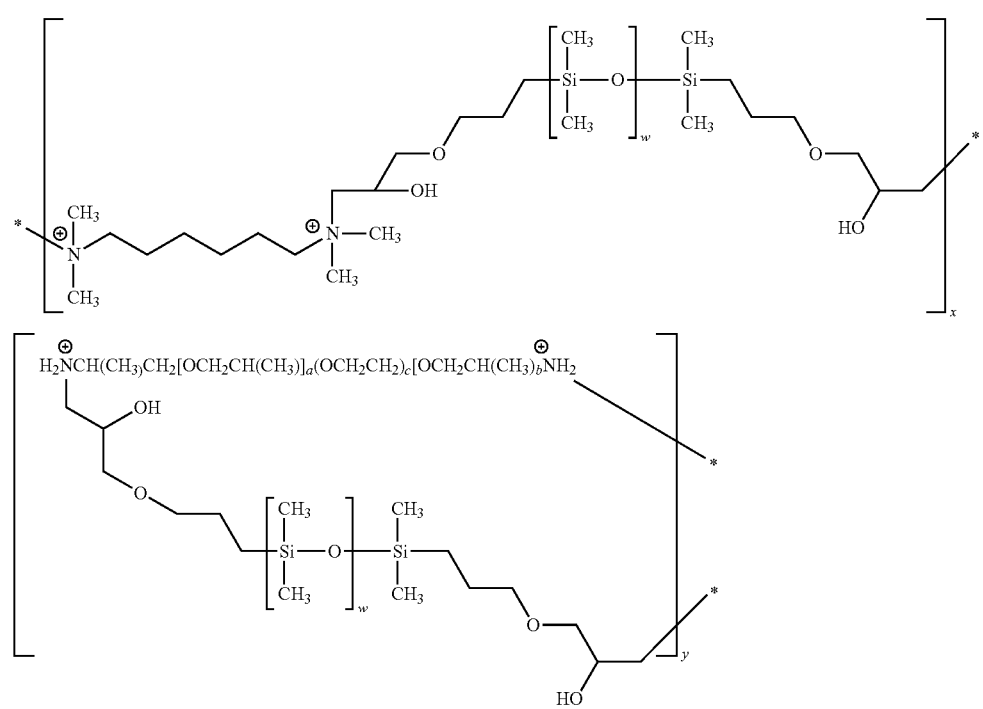

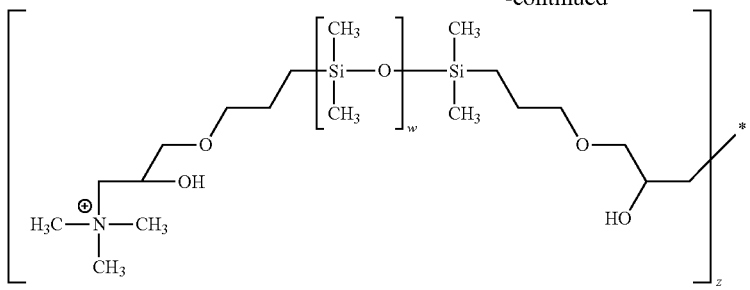

wherein x, y, and z represent mole fractions of the respective components, and hence x+y+z=1;
a+b is less than about 200, preferably a+b is less than about 20, more preferably a+b is less than about 10;
c is less than about 200, preferably c is less than about 100, more preferably c is less than about 50;
w is an integer greater than about 200, preferably greater than about 250, more preferably greater than about 300; preferably less than about 700, more preferably less than about 500; and
$A^-$ is an organic or inorganic anion (for example, the $2A^-$ in the above structure can be laurate and acetate in a 1:1 mole ratio).

Preferably, x is greater than 0.6.

Another more preferred embodiment is the following structure (XIII)

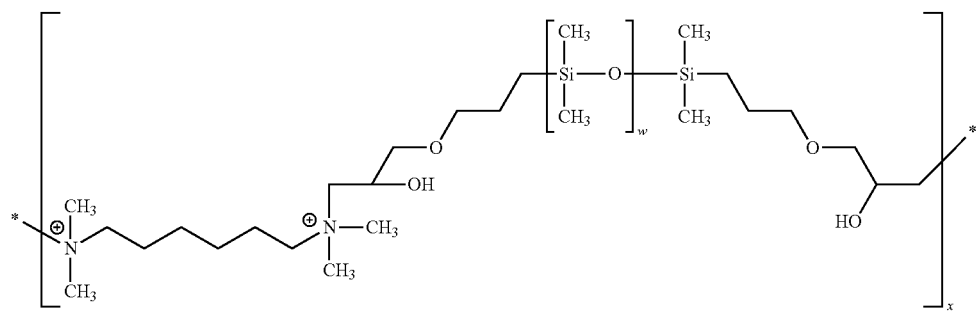

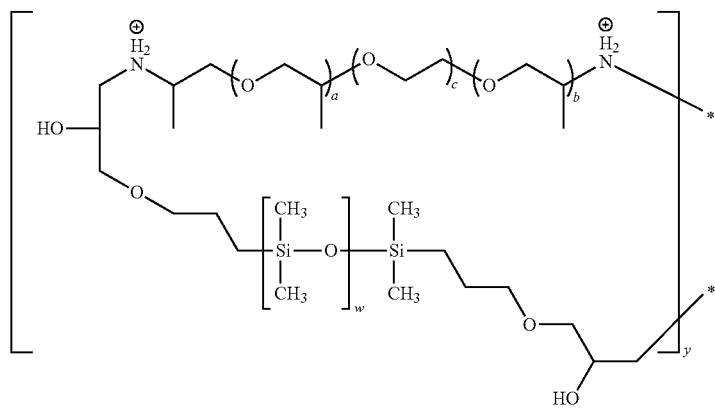

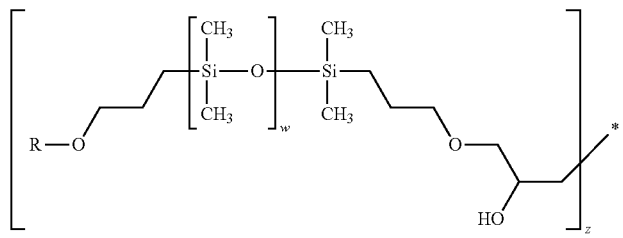

$2A^-$

Where R is selected from the groups:

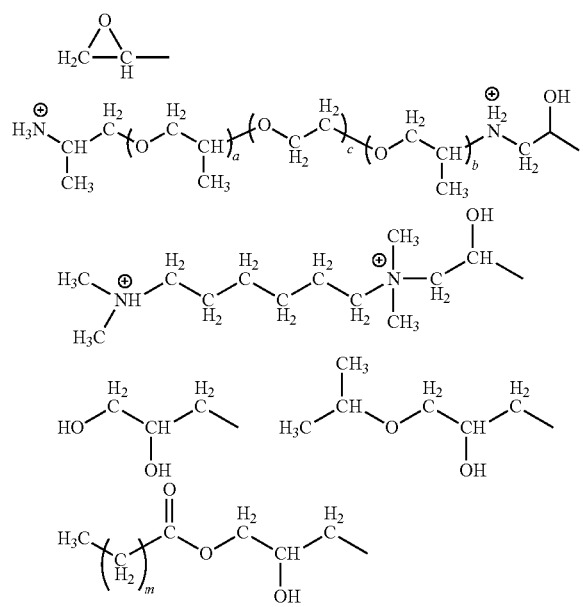

wherein:
x, y, and z represent mole fractions of the respective components, and x+y+z=1;
a+b is an integer from about 2 to about 20;
c is an integer from about 0 to about 200;
w is an integer from about 200 to about 2000, preferably from about 200 to about 800, more preferably from about 250 to about 600; and
A⁻ is an organic or inorganic anion.
Preferably x is greater than 0.6.

Grafted Silicone Copolyol

The composition of the present invention comprises a grafted silicone copolyol. It is believed that; this grafted silicone copolyol can improve the spreadability of the quaternized silicone polymer by reducing the viscosity of the quaternized silicone polymer, and also can stabilize the quaternized silicone polymer in aqueous conditioner matrix. It is also believed that, by such improved spreadability, the composition of the present invention can provide better dry conditioning benefits such as friction reduction and/or prevention of damage with reduced tacky feel. It has been surprisingly found that; the combination of the quaternized silicone polymer, grafted silicone copolyol, and cationic surfactant system comprising di-alkyl quaternized ammonium salt cationic surfactants provides improved friction reduction benefit, compared to a similar combination. Such similar combinations are, for example, a combination in which the grafted silicone copolyol is replaced with end-capped silicone copolyol, and another combination in which the cationic surfactant system is substantially free of di-alkyl quaternized ammonium salt cationic surfactants.

The grafted silicone copolyol is contained in the composition at a level such that the weight % of the grafted silicone copolyol to its mixture with quaternized silicone copolymer is in the range of from about 1% to about 50%, preferably from about 5% to about 40%, more preferably from about 10% to 30%.

The grafted silicone copolyols useful herein are those having a silicone backbone such as dimethicone backbone and polyoxyalkylene substitutions such as polyethylene oxide or/and polypropylene oxide substitutions. The grafted silicone copolyols useful herein have an HLB value of preferably from about 5 to about 17, more preferably from about 8 to about 17, still more preferably from about 8 to about 12. The grafted silicone copolyols having the same INCI name have a variety of the weight ratio, depending on the molecular weight of the silicone portion and the number of the polyethylene oxide or/and polypropylene oxide substitutions.

Highly preferred commercially available grafted dimethicone copolyols include, for example: those having a tradename Silsoft 430 having an HLB value of from about 9 to about 12 (INCI name "PEG/PPG-20/23 dimethicone") available from GE; those having a tradename Silsoft 475 having an HLB value of from about 13 to about 17 (INCI name "PEG-23/PPG-6 dimethicone"); those having a tradename Silsoft 880 having an HLB value of from about 13 to about 17 (INCI name "PEG-12 dimethicone"); those having a tradename Silsoft 440 having an HLB value of from about 9 to about 12 (INCI name "PEG-20/PPG-23 dimethicone"); those having a tradename DC5330 (INCI name "PEG-15/PPG-15 dimethicone") available from Dow Corning. Among them, highly preferred are those having a tradename Silsoft 430 having an HLB value of from about 9 to about 12 (INCI name "PEG/PPG-20/23 dimethicone") available from GE Silicone.

The above quaternized silicone polymer and the grafted silicone copolyol are preferably mixed and emulsified by a emulsifying surfactant, prior to incorporating them into a gel matrix formed by cationic surfactants and high melting point fatty compounds. It is believed that, this pre-mixture can improve behavior of the quaternized silicone polymer and the grafted silicone copolyol, for example, increase the stability and reduce the viscosity to form more homogenized formulation together with the other components. Such emulsifying surfactant can be used at a level of preferably 0.001% to 1.5%, more preferably 0.005% to 1.0%, still more preferably 0.01% to 0.5% by the weight of the composition. Such surfactants are preferably nonionic, and have an HLB value of preferably from about 2 to about 15, more preferably from about 3 to about 14, still more preferably from about 3 to about 10. Commercially available example of highly preferred emulsifying surfactant is nonionic surfactant having an INCI name C12-C14 Pareth-3 having an HLB value of about 8 supplied from NIKKO Chemicals Co., Ltd. with tradename NIKKOL BT-3.

Cationic Surfactant System

The composition of the present invention comprises a cationic surfactant system comprising a dialkyl quaternized ammonium salt cationic surfactant. The cationic surfactant system can be one cationic surfactant or a mixture of two or more cationic surfactants. Preferably, the cationic surfactant system is a mixture of dialkyl quaternized ammonium salt cationic surfactant and monoalkyl quaternized ammonium salt cationic surfactant. The cationic surfactant system is included in the composition at a level by weight of from about 0.1% to about 10%, preferably from about 0.5% to about 8%, more preferably from about 0.8% to about 5%, still more preferably from about 1.0% to about 4%, in view of balance among ease-to-rinse feel, rheology and wet conditioning benefits.

Dialkyl Quaternized Ammonium Salt Cationic Surfactant

The cationic surfactant system of the present invention comprises a dialkyl quaternized ammonium salt cationic surfactant. It is believed that the dialkyl quaternized ammonium salt cationic surfactant can provide easy-to rinse feel, compared to monoalkyl quaternized ammonium salt cationic surfactants.

The dialkyl quaternized ammonium salt cationic surfactants useful herein are those having two long alkyl chains having 5-30 carbon atoms. Such dialkyl quaternized ammonium salt cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride. Such dialkyl quaternized ammonium salt cationic surfactants also include, for example, asymmetric dialkyl quaternized ammonium salt cationic surfactants.

Among a variety of dialkyl quaternized ammonium salt cationic surfactant, preferred are asymmetric dialkyl quaternized ammonium salt cationic surfactants. It is believed that the asymmetric dialkyl quaternized ammonium salt cationic surfactant can provide easy-to-rinse feel, compared to symmetric dialkyl quaternized ammonium salt cationic surfactants. The asymmetric dialkyl quaternized ammonium salt cationic surfactants useful herein are those having the formula (I):

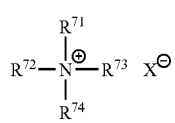

(I)

wherein $R^{71}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; $R^{72}$ is selected from an alkyl group of from 5 to 12 carbon atoms or an aromatic, alkoxy, polyoxyalkylene, alkylamido, hydroxyalkyl, aryl or alkylaryl group having up to about 12 carbon atoms; $R^{73}$ and $R^{74}$ are independently selected from an alkyl group of from 1 to about 4 carbon atoms or an aromatic, alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether linkages, and other groups such as amino groups. The longer chain alkyl groups, e.g., those of about 12 carbons, or higher, can be saturated or unsaturated and/or straight or branched. Preferably, $R^{71}$ is selected from a non-functionalized alkyl group of from 12 to 30 carbon atoms, preferably from 16 to 22 carbon atoms, more preferably 18 to 22 carbon atoms, still more preferably 18 carbon atoms; $R^{72}$ is selected from a non-functionalized alkyl group of from 5 to 12 carbon atoms, more preferably from 6 to 10 carbon atoms, still more preferably 8 carbon atoms; $R^{73}$ and $R^{74}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof. More preferably, $R^{71}$ is a straight, saturated non-functionalized alkyl group, and $R^{72}$ is a branched saturated non-functionalized alkyl group. Still more preferably, the branched group of $R^{72}$ is a straight, saturated alky group of from 1 to 4 carbon atoms, even more preferably 2 carbon atoms.

Nonlimiting examples of preferred asymmetric dialkyl quaternized ammonium salt cationic surfactants include: stearyl ethylhexyl dimonium methosulfate available, for example, with tradename Arquad HTL8-MS from Akzo Nobel having the following structure:

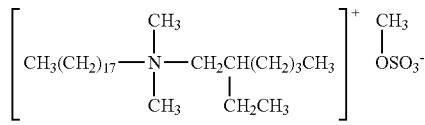

Monoalkyl Quaternized Ammonium Salt Cationic Surfactants

The composition of the present invention preferably contains monoalkyl quaternized ammonium salt cationic surfactants in combination with the above dialkyl quaternized ammonium salt cationic surfactants. The monoalkyl quaternized ammonium salt cationic surfactants can be included in the composition at a level such that the wt % of the monoalkyl quaternized ammonium salt in the cationic surfactant system is in the range of preferably from about 50% to about 90%, more preferably from about 55% to about 70% in view of balance between ease-to-rinse feel and wet conditioning benefits. The use of higher level of dialkyl quaternized ammonium salts tends to lead to reduced wet conditioning benefits such as reduced slippery feel, while the use of lower level of dialkyl quaternized ammonium salts tends to lead to reduced ease-to-rinse feel. In such case, the dialkyl quaternized ammonium salt cationic surfactants, preferably asymmetric dialkyl quaternized ammonium salt cationic surfactants, are used at a level such that the wt % of the dialkyl quaternized ammonium salt cationic surfactants in the cationic surfactant system is in the range of preferably from about 10% to about 50%, more preferably from about 30% to about 45%. It is believed that the use of asymmetric dialkyl quaternized ammonium salt cationic surfactants in combination with monoalkyl quaternized ammonium salt cationic surfactants at the above specific ratio can provide dry friction reduction.

The monoalkyl quaternized ammonium salt cationic surfactants useful herein are those having one long alkyl chain which has from 12 to 22 carbon atoms, preferably from 16 to 22 carbon atoms, more preferably C18-22 alkyl group, in view of providing balanced wet conditioning benefits. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms. Such mono-alkyl cationic surfactants include, for example, mono-alkyl quaternary ammonium salts and mono-alkyl amines. Mono-alkyl quaternary ammonium salts include, for example, those having a non-functionalized long alkyl chain and those having a functionalized long alkyl chain such as those having an ester-linkage. Mono-alkyl amines include, for example, mono-alkyl amidoamines and salts thereof.

It is believed that; mono-alkyl cationic surfactants having a longer alkyl group provide improved deposition on the hair, thus can provide improved conditioning benefits such as improved softness on dry hair, compared to cationic surfactant having a shorter alkyl group. It is also believed that such cationic surfactants can provide reduced irritation, compared to cationic surfactants having a shorter alkyl group.

It is also believed that the use of alkylsulfate such as methosulfate and ethosulfate as a salt-forming anion may be able to provide better conditioning benefits especially wet conditioning benefits, compared to other salt-forming anions.

Mono-long alkyl quaternized ammonium salts useful herein are those having the formula (II):

(II)

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 22 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Nonlimiting examples of such mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt.

Mono-alkyl amines are also suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al. These amines can also be used in combination with acids such as λ-glutamic acid, lactic acid, hydrochloric acid, malic acid, succinic acid, acetic acid, fumaric acid, tartaric acid, citric acid, λ-glutamic hydrochloride, maleic acid, and mixtures thereof; more preferably λ-glutamic acid, lactic acid, citric acid. The amines herein are preferably partially neutralized with any of the acids at a molar ratio of the amine to the acid of from about 1:0.3 to about 1:2, more preferably from about 1:0.4 to about 1:1.

High Melting Point Fatty Compound

The high melting point fatty compound useful herein have a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are preferably used in the composition of the present invention. The fatty alcohols useful herein are those having from about 14 to about 30 carbon atoms, preferably from about 16 to about 22 carbon atoms. These fatty alcohols are saturated and can be straight or branched chain alcohols. Preferred fatty alcohols include, for example, cetyl alcohol, stearyl alcohol, behenyl alcohol, and mixtures thereof.

High melting point fatty compounds of a single compound of high purity are preferred. Single compounds of pure fatty alcohols selected from the group of pure cetyl alcohol, stearyl alcohol, and behenyl alcohol are highly preferred. By "pure" herein, what is meant is that the compound has a purity of at least about 90%, preferably at least about 95%. These single compounds of high purity provide good rinsability from the hair when the consumer rinses off the composition.

The high melting point fatty compound is included in the composition at a level of from about 1% to about 20%, preferably from about 3% to about 10%, more preferably from about 4% to about 8% by weight of the composition, in view of providing improved conditioning benefits such as slippery feel during the application to wet hair, softness and moisturized feel on dry hair.

Gel Matrix

The composition of the present invention comprises a gel matrix. The gel matrix comprises a cationic surfactant, a high melting point fatty compound, and an aqueous carrier.

The gel matrix is suitable for providing various conditioning benefits such as slippery feel during the application to wet hair and softness and moisturized feel on dry hair. In view of providing the above gel matrix, the cationic surfactant and the high melting point fatty compound are contained at a level such that the weight ratio of the cationic surfactant to the high melting point fatty compound is in the range of, preferably from about 1:1 to about 1:10, more preferably from about 1:1 to about 1:6.

For forming gel matrix, it is preferred to prepare the composition by the following method:

Water is typically heated to at least about 70° C., preferably between about 80° C. and about 90° C. The cationic surfactant and the high melting point fatty compound are combined with the water to form a mixture. The temperature of the mixture is preferably maintained at a temperature higher than both the melting temperature of the cationic surfactant and the melting temperature of the high melting point fatty compound, and the entire mixture is homogenized. After mixing until no solids are observed, the mixture is gradually cooled (e.g., at a rate of from about 1° C./minute to about 5° C./minute) to a temperature below 60° C., preferably less than about 55° C. During this gradual cooling process, a significant viscosity increase is observed at between about 55° C. and about 75° C. This indicates the formation of gel matrix. The high molecular weight water-soluble cationic polymer can be added to the mixture with agitation at about 55° C., or prior to the cooling down. Additional components are then combined with the gel matrix, and cooled to room temperature.

Preferably, the present invention comprises, by weight of the hair care composition, from about 60% to about 99%, preferably from about 70% to about 95%, and more preferably from about 80% to about 95% of a gel matrix, to which optional ingredients such as silicones can be added. The composition containing the above amount of gel matrix is typically characterized by rheology at 950s-1 of from about 40 Pa to about 600 Pa, preferably from about 50 Pa to about 500 Pa, and more preferably from about 70 Pa to about 400 Pa, as measured at 26.7° C., by means of TA AR1000 rheometer at shear rate from 0.1 s-1 to 1100s-1 with the duration of 1 minutes. Although the composition of the present invention can contain a thickening polymer, the composition of the present invention can have the above rheology with the presence of any thickening polymer.

Aqueous Carrier

The conditioning composition of the present invention comprises an aqueous carrier. The level and species of the carrier are selected according to the compatibility with other components, and other desired characteristic of the product.

The carrier useful in the present invention includes water and water solutions of lower alkyl alcohols and polyhydric alcohols. The lower alkyl alcohols useful herein are monohydric alcohols having 1 to 6 carbons, more preferably ethanol and isopropanol. The polyhydric alcohols useful herein include propylene glycol, hexylene glycol, glycerin, and propane diol.

Preferably, the aqueous carrier is substantially water. Deionized water is preferably used. Water from natural sources including mineral cations can also be used, depending on the desired characteristic of the product. Generally, the compositions of the present invention comprise from about 20% to about 99%, preferably from about 30% to about 95%, and more preferably from about 80% to about 95% water.

Silicone Copolymer Emulsion

Compositions of the present invention also comprise a silicone copolymer emulsion with an internal phase viscosity of greater than about $100 \times 10^6$ mm$^2$/s, in view of providing clean feel. It is also believed that this silicone copolymer emulsion can provide body/fullness to hair. Additionally, it is believed that this silicone copolymer emulsion, when used together with the above quaternized silicone polymer and grafted silicone copolyol, can form a film on hair which provides enhanced clean feel. It is also believed that this silicone copolymer emulsion additionally provides body/fullness to hair, together with the above quaternized silicone polymer and grafted silicone copolyol, by forming a film on hair. The silicone copolymer emulsion is present in an amount of from about 0.1% to about 15%, preferably from about 0.3% to about 10%, and more preferably from about 0.5% to about 5%, by weight of the composition. When included, it is also preferred that the silicone copolymer emulsion is present at a level such that the wt. % of the silicone copolymer emulsion in its mixture with the quaternized silicone polymer and the grafted silicone copolyol is in the range of from about 10% to 300%, more preferably from about 20% to about 200%, still more preferably from about 40% to about 400%.

The silicone copolymer emulsion has a viscosity at 25° C. of greater than about $100 \times 10^6$ mm$^2$/s, preferably greater than about $120 \times 10^6$ mm$^2$/s, more preferably greater than about $150 \times 10^6$ mm$^2$/s. The silicone copolymer emulsion has a viscosity at 25° C. of, preferably less than about $1000 \times 10^6$ mm$^2$/s, more preferably less than about $500 \times 10^6$ mm$^2$/s, and even more preferably less than about $300 \times 10^6$ mm$^2$/s. To measure the internal phase viscosity of the silicone copolymer emulsion, one must first break the polymer from the emulsion. By way of example, the following procedure can be used to break the polymer from the emulsion: 1) add 10 grams of an emulsion sample to 15 milliliters of isopropyl alcohol; 2) mix well with a spatula; 3) decant the isopropyl alcohol; 4) add 10 milliliters of acetone and knead polymer with spatula; 5) decant the acetone; 6) place polymer in an aluminum container and flatten/dry with a paper towel; and 7) dry for two hours in an 80° C. The polymer can then be tested using any known rheometer, such as, for example, a CarriMed, Haake, or Monsanto rheometer, which operates in the dynamic shear mode. The internal phase viscosity values can be obtained by recording the dynamic viscosity (n') at a $9.900 \times 10^{-3}$ Hz frequency point. The average particle size of the emulsions is preferably less than about 1 micron, more preferably less than about 0.7 micron.

The silicone copolymer emulsions of the present invention comprise a silicone copolymer, at least one surfactant, and water.

The silicone copolymer results from the addition reaction of the following two materials in the presence of a metal containing catalyst:

(a) a polysiloxane with reactive groups on both termini, represented by formula (III)

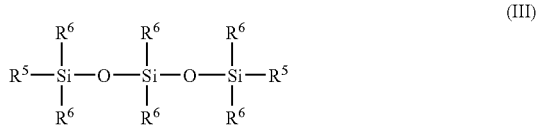

(III)

wherein:

$R^5$ is a group capable of reacting by chain addition reaction such as, for example, a hydrogen atom, an aliphatic group with ethylenic unsaturation (i.e., vinyl, allyl, or hexenyl), a hydroxyl group, an alkoxyl group (i.e., methoxy, ethoxy, or propoxy), an acetoxyl group, or an amino or alkylamino group; preferably, $R^5$ is hydrogen or an aliphatic group with ethylenic unsaturation; more preferably, $R^5$ is hydrogen;

$R^6$ is alkyl, cycloalkyl, aryl, or alkylaryl and may include additional functional groups such as ethers, hydroxyls, amines, carboxyls, thiols esters, and sulfonates; preferably, $R^6$ is methyl. Optionally, a small mole percentage of the groups may be reactive groups as described above for $R^5$, to produce a polymer which is substantially linear but with a small amount of branching. In this case, preferably the level of $R^6$ groups equivalent to $R^5$ groups is less than about 10% on a mole percentage basis, and more preferably less than about 2%;

n is a whole number such that the polysiloxane of formula (III) has a viscosity of from about 1 mm$^2$/s to about $1 \times 10^6$ mm$^2$/s;

and, (b) at least one silicone compound or non-silicone compound comprising at least one or at most two groups capable of reacting with the $R_5$ groups of the polysiloxane in formula (III); preferably, the reactive group is an aliphatic group with ethylenic unsaturation.

The metal containing catalysts used in the above described reactions are often specific to the particular reaction. Such catalysts are known in the art. Generally, they are materials containing metals such as platinum, rhodium, tin, titanium, copper, lead, etc.

The mixture used to form the emulsion also contains at least one surfactant. This can include non-ionic surfactants, cationic surfactants, anionic surfactants, alkylpolysaccharides, amphoteric surfactants, and the like. The above surfactants can be used individually or in combination.

An exemplary method of making the silicone copolymer emulsions described herein comprises the steps of 1) mixing materials (a) described above with material (b) described above, followed by mixing in an appropriate metal containing catalyst, such that material (b) is capable of reacting with material (a) in the presence of the metal containing catalyst; 2) further mixing in at least one surfactant and water; and 3)

emulsifying the mixture. Methods of making such silicone copolymer emulsions are disclosed in U.S. Pat. No. 6,013,682; PCT Application No. WO01/58986 A1; and European Patent Application No. EP0874017 A2.

Commercially available example of highly preferred silicone copolymer emulsion is an emulsion of about 60-70% of divinyldimethicone/dimethicone copolymer having an internal phase viscosity of minimum $120 \times 10^6$ mm$^2$/s, available from Dow Corning with a tradename HMW2220.

Additional Components

The composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: low melting point oils having a melting point of less than 25° C. including, for example, unsaturated fatty alcohols such as oleyl alcohol and ester oils such as pentaerythritol ester oils; cationic conditioning polymers including, for example, cationic celluloses and cationic guar gums; polyethylene glycols; other conditioning agents such as hydrolysed collagen with tradename Peptein 2000 available from Hormel, vitamin E with tradename Emix-d available from Eisai, panthenol available from Roche, panthenyl ethyl ether available from Roche, hydrolysed keratin, proteins, plant extracts, and nutrients; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; perfumes; and sequestering agents, such as disodium ethylenediamine tetraacetate; ultraviolet and infrared screening and absorbing agents such as octyl salicylate; and antidandruff agents such as zinc pyrithione and salicylic acid.

Product Forms

The hair care compositions can be formulated into a variety of product forms, including shampoos, conditioners (both rinse-off and leave-on versions), styling products, and the like. In one embodiment, the hair care compositions include only hair conditioners and do not include shampoos or styling products.

The conditioning compositions of the present invention can be in the form of rinse-off products or leave-on products, and can be formulated in a wide variety of product forms, including but not limited to creams, gels, emulsions, mousses and sprays.

The conditioning composition of the present invention is especially suitable for rinse-off hair conditioner. Such compositions are preferably used by following steps:

(i) after shampooing hair, applying to the hair an effective amount of the conditioning compositions for conditioning the hair; and (ii) then rinsing the hair.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

[Compositions]

| Components | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|
| Quaternized silicone polymer-1 *1 | 1.6 | — | — | 1.6 | 1.2 | — | — | 1.35 | — |
| Quaternized silicone polymer-2 *2 | — | 1.6 | 8.0 | — | — | 0.9 | 1.6 | — | 1.6 |
| Nonionic surfactant *3 | 0.04 | 0.04 | — | 1.5 | 0.12 | 0.01 | 0.04 | 0.04 | 0.04 |
| Silicone copolyol-1 *4 | 0.36 | 0.4 | — | 0.36 | 0.6 | 0.1 | 0.36 | 0.30 | 0.36 |
| Silicone copolyol-2 *5 | — | — | 2.0 | — | — | — | — | — | — |
| Silicone copolymer emulsion *6 | 1.64 | 1.64 | 4.0 | 2.0 | 1.2 | 1.0 | 2.0 | 1.3 | 2.0 |
| Dialkyl dimethyl ammonium chloride-1 *7 | 0.64 | 0.64 | 0.64 | 0.64 | 0.48 | 0.64 | — | 0.91 | — |
| Dialkyl dimethylammonium chloride-2 *8 | — | — | — | — | — | — | 0.64 | — | 0.224 |
| Behenyl trimethyl ammonium chloride | 0.96 | 0.96 | 0.96 | 0.96 | 1.12 | 0.96 | 0.96 | 1.37 | 1.377 |
| Isopropyl alcohol | 0.236 | 0.236 | 0.236 | 0.236 | 0.28 | 0.236 | 0.236 | 0.343 | 0.34 |
| Cetyl alcohol | 1.30 | 1.30 | 1.30 | 1.30 | 1.30 | 1.30 | 1.30 | 1.857 | 1.30 |
| Stearyl alcohol | 3.25 | 3.25 | 3.25 | 3.25 | 3.25 | 3.25 | 3.25 | 4.643 | 3.25 |
| Preservatives | 0.53 | 0.53 | 0.53 | 0.53 | 0.53 | 0.53 | 0.53 | 0.53 | 0.53 |
| Perfume | 0.4 | 0.4 | 0.4 | 0.4 | 0.35 | 0.25 | 0.25 | 0.25 | 0.4 |
| Panthenol | 0.05 | 0.05 | — | 0.05 | 0.05 | — | 0.05 | 0.05 | 0.05 |
| Panthenyl ethyl ether | 0.03 | 0.03 | — | 0.03 | 0.03 | — | 0.05 | 0.05 | 0.03 |
| Deionized Water | q.s. to 100% | | | | | | | | |

Definitions of Components

*1 Quaternized silicone polymer-1: having the structure (XII), with x = 0.8, y = 0.1, z = 0.1, a + b = 6, c = 39, and w = 350, neat
*2 Quaternized silicone polymer-2: having the structure (XIII), with x = 0.8, y + z = 0.2, a + b = 6, c = 39, and w = 350, neat
*3 Nonionic surfactant: NIKKOL BT-3 available from NIKKO Chemical
*4 Silicone copolyol-1: Silsoft 430 available from GE Silicone
*5 Silicone copolyol-2: Silsoft 880 available from GE Silicone
*6 Silicone copolymer emulsion-1: an emulsion of about 60-70% of divinyldimethicone/dimethicone copolymer having an internal phase viscosity of minimum $120 \times 10^6$ mm$^2$/s, available from Dow Corning with a tradename HMW2220
*7 Dialkyl dimethyl ammonium chloride-1: 84% Aqueous mixture of Hydrogenated tallowalkyl (2-ethylhexyl) dimethyl quaternary ammonium methosulfate available with a tradename Arquad HTL8-MS from Akzo Nobel
*8 Dialkyl dimethyl ammonium chloride-2: Distearyl dimethylammonium Chloride available from Goldschmidt Method of Preparation The conditioning compositions of "Ex. 1" through "Ex. 9" as shown above can be prepared by any conventional method well known in the art. They are suitably made as follows:

Cationic surfactants and high melting point fatty compounds are added to water with agitation, and heated to about 80° C. The mixture is cooled down to about 55° C. Quaternized silicone polymers, silicone copolyols, and if included, nonionic surfactants are mixed to form silicone pre-mixture. This silicone pre-mixture is added with agitation to the above mixture of cationic surfactant, high melting fatty compounds and water. If included, other components such as perfumes and preservatives are added to the mixture with agitation. Then the mixture is cooled down to room temperature.

Examples 1 through 9 are hair conditioning compositions of the present invention which are particularly useful for rinse-off use. The embodiments disclosed and represented by the previous "Ex. 1" through "Ex. 9" have many advantages. For example, they provide improved conditioning benefits such as smooth feel and reduced friction in conditioning compositions using dialkyl quaternized ammonium salt cationic surfactants. Additionally, they can provide clean feel and/or reduced tacky/heavy feel, while providing such improved conditioning benefits.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair conditioning composition comprising by weight:
   (a) from 0.1% to 15% of a silicone polymer containing quaternary groups wherein said silicone polymer comprises silicone blocks with greater than 200 siloxane units wherein the quaternized silicone polymer has the following structure (XII):

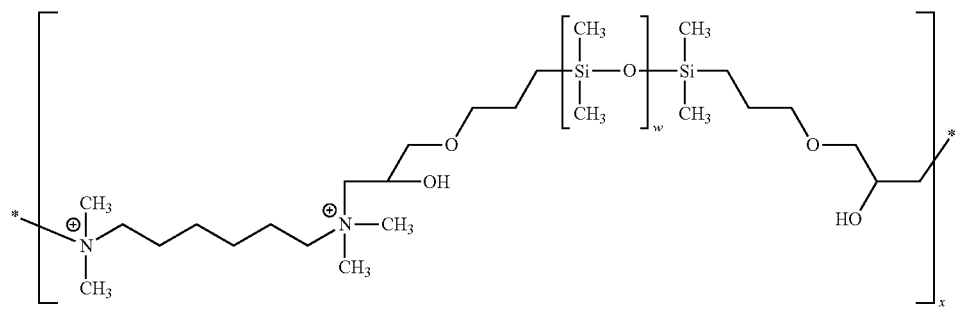

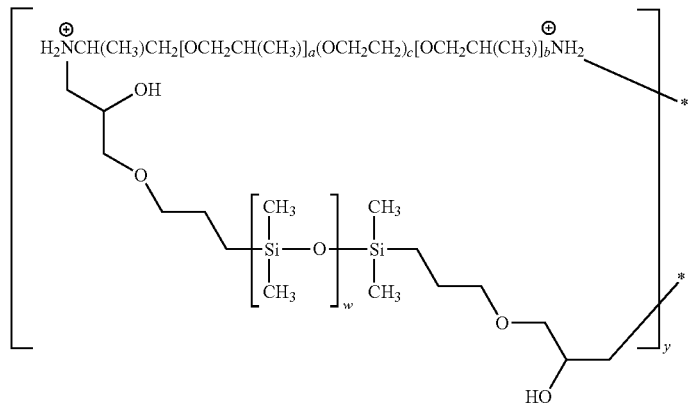

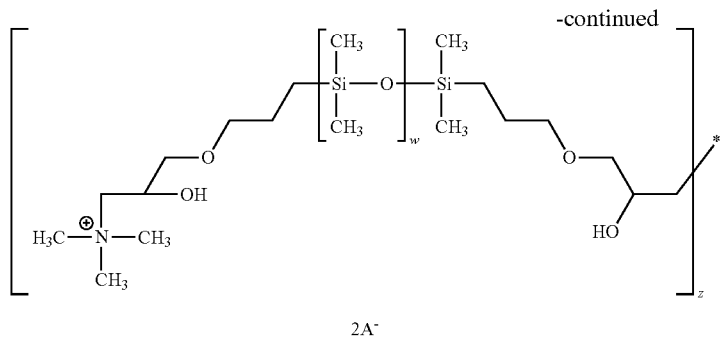

2A⁻ wherein x, y, and z represent mole fractions of the respective components, and hence x+y+z=1;
a+b is less than 200;
c is less than 200;
w is an integer greater than 200; and
A⁻ is an organic or inorganic anion;

(b) a grafted silicone copolyol having an HLB value of from 9 to 12 and having the INCI name PEG/PPG-20/23 dimethicone at a level such that the weight % of the grafted silicone copolyol in its mixture with the quaternized silicone polymer is in the range of from 1% to 50%;

(c) from 0.1% to 10% by weight of the composition of a cationic surfactant system comprising a dialkyl quaternized ammonium salt cationic surfactant wherein the dialkyl quaternized ammonium salt cationic surfactant is stearyl ethylhexyl dimonium methosulfat having the following structure:

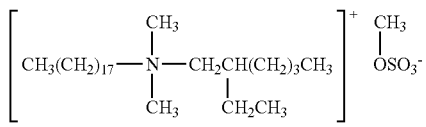

(d) from 1% to 20% by weight of the composition of a high melting point fatty compound wherein the high melting point fatty compound has a melting point of 25° C. or higher and wherein the high melting point compound is cetyl alcohol and stearyl alcohol; and (e) an aqueous carrier wherein the aqueous carrier is water.

2. The hair conditioning composition of claim 1 wherein the weight % of the grafted silicone copolyol in its mixture with the quaternized silicone polymer is in the range of from 5% to 40%.

3. The hair conditioning composition of claim 1 wherein the weight % of the grafted silicone copolyol in its mixture with the quaternized silicone polymer is in the range of from 10% to 30%.

4. The hair conditioning composition of claim 1 further comprising a nonionic surfactant, and wherein the quaternized silicone polymer, the grafted silicone copolyol, and the nonionic surfactant are mixed prior to the incorporation into a gel matrix formed by the cationic surfactant and the high melting point fatty compound wherein the high melting point fatty compound has a melting point of 25° C. or higher.

5. The hair conditioning composition of claim 1 wherein the cationic surfactant system further comprises a monoalkyl quaternized ammonium salt cationic surfactant, wherein the monoalkyl quaternized ammonium salt cationic surfactant is behenyl trimethyl ammonium salt from at a level such that the wt % of the monoalkyl quaternized ammonium salt cationic surfactant in the cationic surfactant system is in the range of from 50% to 90%.

6. The hair conditioning composition of claim 1 further containing from 0.1% to 15% of a silicone copolymer emulsion with an internal phase viscosity of greater than $100 \times 10^6$ mm²/s.

7. The hair conditioning composition of claim 1 wherein the composition is substantially free of anionic surfactants and anionic polymers.

* * * * *